United States Patent
Gabor et al.

(10) Patent No.: US 11,261,218 B2
(45) Date of Patent: Mar. 1, 2022

(54) **SPECIES OF GENUS *PSEUDOMONAS***

(71) Applicant: BRAIN AG, Zwingenberg (DE)

(72) Inventors: Esther Gabor, Zwingenberg (DE);
Renate Schulze, Bensheim (DE);
Arnulf Kletzin, Darmstadt (DE)

(73) Assignee: BRAIN AG, Zwingenberg (DE)

( * ) Notice: Subject to any disclaimer, the term of this patent is extended or adjusted under 35 U.S.C. 154(b) by 0 days.

(21) Appl. No.: 16/646,458

(22) PCT Filed: Sep. 17, 2018

(86) PCT No.: PCT/EP2018/075071
§ 371 (c)(1),
(2) Date: Mar. 11, 2020

(87) PCT Pub. No.: WO2019/057664
PCT Pub. Date: Mar. 28, 2019

(65) Prior Publication Data
US 2020/0216503 A1 Jul. 9, 2020

(51) Int. Cl.
*C12N 1/20* (2006.01)
*C07K 14/21* (2006.01)
*C22B 3/18* (2006.01)
*C12R 1/38* (2006.01)

(52) U.S. Cl.
CPC .............. *C07K 14/21* (2013.01); *C12N 1/205* (2021.05); *C22B 3/18* (2013.01); *C12R 2001/38* (2021.05)

(58) Field of Classification Search
CPC ........... C07K 14/21; C12N 1/20; C12N 1/205
See application file for complete search history.

(56) References Cited

FOREIGN PATENT DOCUMENTS

| EP | 0432935 A1 | 6/1991 |
|---|---|---|
| WO | 2019057664 A1 | 3/2019 |

OTHER PUBLICATIONS

Faramarzi, Mohammad A. et al., "Metal solubilization from metal-containing solid material by cyanogenic Chromobacterium violaceum". Journal of Biotechnology, 2004, vol. 113, pp. 321-326.
Chi, Tran D. et al., "Bioleaching of gold and copper from waste mobile phone PCBs by using a cyanogenic bacterium", Minerals Engineering, 2011, vol. 24, pp. 1219-1222.

*Primary Examiner* — Tekchand Saidha
(74) *Attorney, Agent, or Firm* — Wolter VanDyke Davis PLLC; Michael Byrne (57) ABSTRACT

The present invention relates to a species of genus *Pseudomonas* identified as *Pseudomonas* BR11571, termed *Candidatus Pseudomonas metallosolvens*, having Accession Deposit Number DSM 32538.

14 Claims, 7 Drawing Sheets
Specification includes a Sequence Listing.

| Accession number | Species name | Strain | | Risk group | Similarity [%] BR11571 |
|---|---|---|---|---|---|
| | | BR11571 | | | 100.00 |
| NZ_CP015852 | Pseudomonas koreensis | CRS05-R5 | | | 97.33 |
| FN554194 | Pseudomonas koreensis | DSM16610T | Type strain | R1 (TRBA 466, 31.03.2017) | 97.19 |
| CP014947 | Pseudomonas koreensis | D26 | | | 96.89 |
| CP000094 | Pseudomonas | Pf0-1 | | | 96.59 |
| FN554206 | Pseudomonas moraviensis | DSM16007 | Type strain | R1 (TRBA 466, 31.03.2017) | 95.85 |
| HG940516 | Pseudomonas helmanticensis | OHA11 | Type strain | R1 (provisional classificaton by DSMZ) | 95.85 |
| HE800470 | Pseudomonas baetica | CECT 7720 | Type strain | R1, t2 (TRBA 466, 31.03.2017) | 95.26 |
| HG764749 | Pseudomonas granadensis | F-278,770 | Type strain | R1 (provisional classification by DSMZ) | 94.22 |
| FN554191 | Pseudomonas jessenii | CIP 105274 | Type strain | R1 (TRBA 466, 31.03.2017) | 93.48 |
| FN554231 | Pseudomonas umsongensis | LMG 21317 | Type strain | R1 (TRBA 466, 31.03.2017) | 93.19 |
| FN554232 | Pseudomonas vancouverensis | ATCC 700688 | Type strain | R1 (TRBA 466, 31.03.2017) | 92.89 |
| FN554171 | Pseudomonas chlororaphis | ATCC 33663 | Type strain | R1 (TRBA 466, 31.03.2017) | 92.74 |
| D86016 | Pseudomonas fluorescens | IAM 12022 | Type strain | R1+, n (TRBA 466, 31.03.2017) | 90.67 |
| AB039455 | Pseudomonas asplenii | NCPPB 1947 | Type strain | R1, p (TRBA 466, 31.03.2017) | 89.63 |
| FN554185 | Pseudomonas fuscovaginae | LMG 2158 | Type strain | R1 (TRBA 466, 31.03.2017) | 89.48 |
| AB039457 | Pseudomonas agarici | NCPPB 2289 | Type strain | R1, p (TRBA 466, 31.03.2017) | 89.33 |
| FN554166 | Pseudomonas abietaniphila | ATCC 700689 | Type strain | R1 (TRBA 466, 31.03.2017) | 85.93 |
| FN554187 | Pseudomonas graminis | LMG 21661 | Type strain | R1 (TRBA 466, 31.03.2017) | 85.93 |
| FN554224 | Pseudomonas rhizosphaerae | LMG 21640 | Type strain | R1 (TRBA 466, 31.03.2017) | 85.48 |
| FN554198 | Pseudomonas lutea | LMG 21974 | Type strain | R1 (TRBA 466, 31.03.2017) | 85.04 |
| AB039386 | Pseudomonas aeruginosa | IFO 12689 | Type strain | R2, ht (TRBA 466, 31.03.2017) | 84.44 |

Fig. 3

| Accession number | Species name | Strain | | Risk group | Similarity [%] BR11571 |
|---|---|---|---|---|---|
| | | BR11571 | | | 100.00 |
| HG764747 | Pseudomonas granadensis | F-278.770 | Type strain | R1 (provisional classificaton by DSMZ) | 97.26 |
| GCF001654515 5295541 bis 5291468 | Pseudomonas koreensis | CRS05-R5 | | | 97.15 |
| FN554737 | Pseudomonas koreensis | LMG21318 | Type strain | R1 (TRBA 466, 31.03.2017) | 97.15 |
| CP014947 | Pseudomonas koreensis | D26 | | | 96.49 |
| HE800504 | Pseudomonas baetica | CECT7720 | Type strain | R1, t2 (TRBA 466, 31.03.2017) | 96.38 |
| FN554743 | Pseudomonas moraviensis | DSM16007 | Type strain | R1 (TRBA 466, 31.03.2017) | 95.94 |
| CP000094 | Pseudomonas | Pf0-1 | | | 95.72 |
| AJ717473 | Pseudomonas vancouverensis | CIP106707 | Type strain | R1 (TRBA 466, 31.03.2017) | 94.74 |
| AJ717447 | Pseudomonas jessenii | CIP105274 | Type strain | R1 (TRBA 466, 31.03.2017) | 94.30 |
| FN554763 | Pseudomonas umsongensis | LMG21317 | Type strain | R1 (TRBA 466, 31.03.2017) | 94.30 |
| FN554754 | Pseudomonas reinekei | CCUG53116 | Type strain | R1 (TRBA 466, 31.03.2017) | 94.08 |
| AJ717433 | Pseudomonas fuscovaginae | LMG2158 | Type strain | R1 (TRBA 466, 31.03.2017) | 94.08 |
| HG940518 | Pseudomonas helmanticensis | OHA11 | Type strain | R1 (provisional classification by DSMZ) | 93.86 |
| AJ717432 | Pseudomonas asplenii | LMG2137 | Type strain | R1, p (TRBA 466, 31.03.2017) | 93.75 |
| FN554741 | Pseudomonas mohnii | CCUG53115 | Type strain | R1 (TRBA 466, 31.03.2017) | 93.31 |
| AJ717451 | Pseudomonas fluorescens | CIP69.13 | Type strain | R1+, n (TRBA 466, 31.03.2017) | 93.31 |
| FN554742 | Pseudomonas moorei | CCUG53114 | Type strain | R1 (TRBA 466, 31.03.2017) | 92.98 |
| FN554755 | Pseudomonas rhizosphaerae | LMG21640 | Type strain | R1 (TRBA 466, 31.03.2017) | 92.00 |
| AJ717416 | Pseudomonas abietaniphila | CIP106708 | Type strain | R1 (TRBA 466, 31.03.2017) | 90.79 |
| AJ717477 | Pseudomonas agarici | LMG 2112 | Type strain | R1, p (TRBA 466, 31.03.2017) | 90.79 |
| AJ717429 | Pseudomonas graminis | CIP 105897 | Type strain | R1 (TRBA 466, 31.03.2017) | 90.02 |
| FN554738 | Pseudomonas lutea | LMG21974 | Type strain | R1 (TRBA 466, 31.03.2017) | 89.36 |
| AJ717442 | Pseudomonas aeruginosa | LMG1242 | Type strain | R2, ht (TRBA 466, 31.03.2017) | 86.95 |

Fig. 4

| Accession number | Species name | Strain | | Risk group | Similarity [%] BR11571 |
|---|---|---|---|---|---|
| | | BR11571 | | | 100.00 |
| HG940517 | Pseudomonas helmanticensis | OHA11 | Type strain | R1 (provisional classificaton by DSMZ) | 96.07 |
| HG764748 | Pseudomonas granadensis | F-278.770 | Type strain | R1 (provisional classificaton by DSMZ) | 93.21 |
| FN554490 | Pseudomonas moraviensis | DSM16007 | Type strain | R1 (TRBA 466, 31.03.2017) | 92.68 |
| FN678357 | Pseudomonas baetica | a390 | Type strain | R1, t2 (TRBA 466, 31.03.2017) | 92.32 |
| CP014947 | Pseudomonas koreensis | D26 | | | 91.79 |
| NZ_CP015852 | Pseudomonas koreensis | CRS05-R5 | | | 90.89 |
| FN554476 | Pseudomonas koreensis | LMG21318 | Type strain | R1 (TRBA 466, 31.03.2017) | 90.54 |
| CP000094 | Pseudomonas | Pf0-1 | | | 89.64 |
| FN554508 | Pseudomonas reinekei | CCUG 53116 | Type strain | R1 (TRBA 466, 31.03.2017) | 89.64 |
| FN554487 | Pseudomonas mohnii | CCUG53115 | Type strain | R1 (TRBA 466, 31.03.2017) | 88.93 |
| FN554489 | Pseudomonas moorei | CCUG53114 | Type strain | R1 (TRBA 466, 31.03.2017) | 88.75 |
| FN554473 | Pseudomonas jessenii | CIP105274 | Type strain | R1 (TRBA 466, 31.03.2017) | 87.86 |
| FN554516 | Pseudomonas umsongensis | LMG 21317 | Type strain | R1 (TRBA 466, 31.03.2017) | 87.86 |
| AB039563 | Pseudomonas agarici | NCPPB 2289 | Type strain | R1, p (TRBA 466, 31.03.2017) | 87.28 |
| FN554517 | Pseudomonas vancouverensis | ATCC 700688 | Type strain | R1 (TRBA 466, 31.03.2017) | 86.79 |
| AB039545 | Pseudomonas fluorescens | IAM 12022 | Type strain | R1+, n (TRBA 466, 31.03.2017) | 84.64 |
| FN554447 | Pseudomonas abietaniphila | ATCC 700689 | Type strain | R1 (TRBA 466, 31.03.2017) | 81.72 |
| FN554467 | Pseudomonas fuscovaginae | LMG 2158 | Type strain | R1 (TRBA 466, 31.03.2017) | 81.36 |
| AB039593 | Pseudomonas asplenii | NCPPB 1947 | Type strain | R1, p (TRBA 466, 31.03.2017) | 81.00 |
| FN554469 | Pseudomonas graminis | LMG 21661 | Type strain | R1 (TRBA 466, 31.03.2017) | 80.97 |
| FN554480 | Pseudomonas lutea | LMG 21974 | Type strain | R1 (TRBA 466, 31.03.2017) | 79.96 |
| FN554510 | Pseudomonas rhizosphaerae | LMG 21640 | Type strain | R1 (TRBA 466, 31.03.2017) | 76.34 |
| AB039607 | Pseudomonas aeruginosa | IFO 12689 | Type strain | R2, ht (TRBA 466, 31.03.2017) | 68.00 |

| Assembly accession | Species name | Strain | Risk group | ANIb [%] BR11571 |
|---|---|---|---|---|
| scaffold BR11571 (BRAIN AG) | | BR11571 | | 100.00 |
| LMG 28168 | Pseudomonas helmanticensis | LMG 28168 (T) | R1 (provisional classification by DSMZ) | 90.96 |
| GCF_000282235.1 | Pseudomonas | GM24 | | 90.48 |
| GCF_000282155.1 | Pseudomonas | GM16 | | 90.46 |
| GCF_000282515.1 | Pseudomonas | GM80 | | 90.42 |
| GCF_000276585.1 | Pseudomonas fluorescens | N2011 | | 90.31 |
| LMG25716_finalassembly | Pseudomonas baetica | LMG25716 (T) | R1, t2 (TRBA 466, 31.03.2017) | 88.31 |
| GCF_001654515.1 | Pseudomonas koreensis | CRS05-R5 | | 87.73 |
| GCF_000514195.1 | Pseudomonas | URIL14-HWK12-I6 | | 87.60 |
| GCA_900105485.1 | Pseudomonas granadensis | LMG 27940 (T) | R1 (provisional classification by DSMZ) | 87.54 |
| GCF_000282275.2 | Pseudomonas | GM30 | | 87.53 |
| GCF_000292795.1 | Pseudomonas fluorescens | R124 | | 87.51 |
| GCF_000512275.1 | Pseudomonas moraviensis | R28-S | | 87.29 |
| GCF_001605965.1 | Pseudomonas koreensis | D26 | | 87.29 |
| GCF_000257605.1 | Pseudomonas | R62 | | 87.24 |
| GCF_000633255.1 | Pseudomonas | H1h | | 87.16 |
| GCF_000282255.1 | Pseudomonas | GM25 | | 86.96 |
| GCF_000012445.1 | Pseudomonas | Pf0-1 | | 86.76 |
| GCF_000316175.1 | Pseudomonas | UW4 | | 84.06 |
| GCA_900104125.1 | Pseudomonas reinekei | BS3776 | | 84.03 |
| GCA_900104905.1 | Pseudomonas jessenii | BS3660 | | 83.98 |
| GCA_900102045.1 | Pseudomonas moorei | BS3775 | | 83.96 |
| GCF_001945365.1 | Pseudomonas reinekei | MT1 | | 83.93 |
| GCA_900105115.1 | Pseudomonas mohnii | DSM 18327 (T) | R1 (TRBA 466, 31.03.2017) | 83.83 |
| GCF_900105285.1 | Pseudomonas umsongensis | BS3657 | | 83.65 |
| GCA_900105825.1 | Pseudomonas vancouverensis | BS3656 | | 83.64 |
| GCF_000237065.1 | Pseudomonas fluorescens | F113 | | 82.09 |
| GCF_000194805.1 | Pseudomonas brassicacearum subsp. brassicacearum | NFM421 | | 82.05 |
| GCF_000397205.1 | Pseudomonas protegens | CHA0 | | 81.14 |
| GCF_000336465.1 | Pseudomonas poae | RE*1-1-14 | | 81.09 |
| GCA_000012265.1 | Pseudomonas protegens | Pf-5 | | 81.02 |
| GCF_000009225.2 | Pseudomonas fluorescens | SBW25 | | 81.01 |
| GCF_000272675.1 | Pseudomonas tolaasii | DSM 19342 (T) | R1, p (TRBA 466, 31.03.2017) | 80.93 |
| GCF_001645105.1 | Pseudomonas marginalis | ICMP 3553 | | 80.92 |
| GCF_000276565.1 | Pseudomonas tolaasii | PMS117 | | 80.90 |
| GCF_001269845.1 | Pseudomonas fluorescens | DSM50090 (T) | R1+, n (TRBA 466, 31.03.2017) | 80.79 |
| GCF_000262325.2 | Pseudomonas fluorescens | A506 | | 80.78 |

Fig. 7

TTGCTCCCTGGATTCAGCGGCGGACGGGTGAGTAATGCCTAGGAATCTGCCTGGTAGTGGGGGACAACGTTTCGAAAGGAACGCTAATACCGCATACGTCCTACGGGAGA
AAGCAGGGGACCTTCGGGCCTTGCGCTATCAGATGAGCCTAGGTCGGATTAGCTAGTTGGTGAGGTAATGGCTCACCAAGGCGACGATCCGTAACTGTCTGAGAGGAT
GATCAGTCACACTGGAACTGAGACACGGTCCAGACTCCTACGGGAGGCAGCAGTGGGGAATATTGGACAAGCCTGATCCAGCAGCCGAAAGCCTAACTCTGTGTGAAG
AAGGTCTTCGGATTGTAAAGCACTTTAAGTTGGGAGGAAGGGCAGTAAATACTTTGCTGTTTTGACGTTACCGACAGAATAAGCACCGGCTAACTCTGTGCCAGC
AGCCGCGGTAATACAGAGGGTGCAAGCGTTAATCGGAATTACTGGGCGTAAAGCGCGCGTAGGTGGTTCGTTAAGTTGAAATGTGAAATCACCCGGGCTCAACCTGGGAAC
TGCATCCAAAACTGGCGAGCTAGAGTATGGTAGAGGGTGGTGGAATTTCCTGTGTAGCGGTGAAATGCGTAGATATAGGAAGGAACACCAGTGGCGAAGGCGACCACCT
GGACTGATACTGACACTGAGGTGCGAAAGCGTGGGGAGCAAACAGGATTAGATACCCTGGTAGTCCACGCCGTAAACGATGTCAACTAGCCGTTGGGAGCTTGAGCTC
TTAGTGGCGCAGCTAACGCATTAAGTTGACCGCCTGGGGAGTACGGCCGCAAGGTTAAAACTCAAATGAATTGACGGGGCCCGCACAAGCGGTGGAGCATGTGGTTTA
ATTCGAAGCAACGCGAAGAACCTTACCAGGCCTTGACATCGAGCGCAACCCTTGTCCTTAGTTACCAGCACGTAATGGTGGGCACTCTAAGGAGACTGCCGGTGACAAACCG
GCTCGTGTCGTGAGATGTTGGGTTAAGTCCCGTAAGTCCCCTTACGGCCCTTACGGCCTACAAATGGTCGGTACAACGGGTTGCCAAGCCGCGAGGTGGAGCTAATCCC
AGGAAGGTGGGGATGACGTCAAGTCATCATGCCCCTTACGGCCCTTACGGCTACACGCCCCTGCCAACTCGCCTGCGCTGAACTCGCCCTGCGCTGAACTCGCCCTGCTACAAATGGTCGGTACAACGGGTTGCCAAGCCGCGAGGTGGAGCTAATCCC
ATAAACCGATCGTAGTCCGGATCGCAGTCTGCAACTCGACTGCGTGAAGTCGGAATCGCTAGTAATCGTGAATCAGAATCGTCACGGTGAATACGTTCCCGGGCCTTGT
ACACACCGCCCGTCACACCATGGGAGTGGGTTGCACCAGAAGTAGCTAGTCTAACCTTCGGGAGGACGGT

SPECIES OF GENUS *PSEUDOMONAS*

CROSS-REFERENCE TO RELATED APPLICATION

This application is a national stage entry of and claims priority to PCT/EP2018/075071, filed Sep. 17, 2018, which is hereby incorporated by reference in its entirety.

FIELD OF INVENTION

The invention relates to a new species of genus *Pseudomonas*, termed *Candidatus Pseudomonas metallosolvens*, the use thereof for the recovery of precious metals from solid materials, a composition containing the new species and an isolated nucleic acid.

BACKGROUND OF THE INVENTION

The recovery of copper from ores by means of cyanide and suitable extractants like guanidine (LIX 7950) or amines (LIX 7820) is known for decades (for example U.S. Pat. No. 3,403,020, 1968). The free cyanide remains in the aqueous phase due to the preferential extraction of $Cu(CN)_3^{2-}$ over $Cu(CN)_4^{3-}$ and $CN^-$ by the extractants. High cyanide levels tend to depress extraction of copper and silver cyanides, but exhibit insignificant effect on extraction of gold, zinc, nickel and iron cyanides. An overview for this technology is provided for example by XIE ET AL in J. Hazardous Materials, Vol. 169, p 333-338 (2009).

While in the past the process for recovering copper and precious metals, in particular gold by using potassium or sodium cyanide has led to huge waste dumps contaminated with poisonous materials, todays processes run in closed cycles and do not have the environmental impact as in the past. Nevertheless, working with cyanides even in closed systems is still dangerous, in particular since a plant typically contains hundred thousands of gallons extractants enriched with cyanide.

For this reason it is not surprising that today methods for biological extraction of ores and waste materials, so-called "bioleaching processes" are of high commercial interest. Usually autotrophic bacteria are used for these purposes which are capable of producing sulfuric acid in which copper forms a soluble sulfate. Nowadays, about 24% of world-wide copper production uses bioleaching processes operating at low pH values of less than 3 and using carbon dioxide as the sole carbon source for the microorganisms. Beside the fact that these processes run rather slowly, they typically do not work for precious metals like gold, silver or platinum, since these metals are insoluble in sulfuric acid.

In this context reference is made to European patents EP 0432935 B1 and EP 0695809 A1 (GEOBIOTICS) disclosing processes to recover and reconcentrate gold from its ores. The processes involve a bioleaching step preferably using algae or blue-green cyanobacteriae as suitable microorganisms for producing and releasing hydrocyanic acid to form gold complexes. Among various other microorganisms *Bacillus megaterium* and some *Pseudomonas* sp. are mentioned. The technical teaching of this piece of prior art, however, is directed to recover gold from ores, i.e. a natural, primary resource that only contains traces of precious metals of <10 ppm. The document does not provide any guidance with regard to the recovery of precious metals from manmade mineralic materials such as industrial residues and waste materials containing precious metals in significantly higher amounts than ores.

Another well-known microorganism for recovering gold for example from electronic scrap is *Chromobacterium violaceum*. Unfortunately, the efficacy of this bacterium in the leaching process is found to be rather poor [see CAMPBELL ET AL, J. Industrial Microbiology & Biotechnology, 26, p 134-139 (2001) or FARAMARZI ET AL, J. Biotechnology. 113, 321-326 (2004)]. Furthermore, *Chromobacterium violaceum* is a pathogenic microorganism that can cause severe infections in humans, therefore being classified as risk group 2. This fact compromises the use of this organism in an economically viable, industrial set-up.

A particular drawback of using industrial residues and waste materials, however, is their generally high amount of toxic metals, in particular lead, chromium, cadmium, arsenic or silver since most microorganisms capable for biomining or bioleaching are rather sensitive to them, in particular when present in high dosages.

Therefore, it has been the object of the present invention to provide a group of microorganisms for recovering precious metals like for example gold, silver, platinum and/or palladium from so-called secondary resources, which means industrial residuals or waste materials, often contaminated with polychlorinated biphenyl (PCB) and other organic material, comprising increased amounts of the target metals, typically in the range of up to 0.2% or more.

Another object of the present invention is it to provide a group of microorganisms tolerating poisonous metals such as lead, chromium, cadmium and silver also in high dosages as they are typical for industrial residues and waste materials.

Finally, for safety reasons, it has been the object of the present invention to provide a group of microorganisms belonging to risk group 1, since in the future no technical process will pass approval from governmental health and risk authorities involving microorganisms belonging to risk class 2 or even higher.

These and other objects of the present invention will become apparent as a detailed description of the representative embodiments is disclosed infra.

DESCRIPTION OF THE INVENTION

This object is solved by claim 1 of the present invention, which is directed to a species of genus *Pseudomonas* termed *Candidatus Pseudomonas metallosolvens* (in the following: *Pseudomonas* BR11571) having Accession Deposit Number DSM 32538.

Surprisingly the inventors have found that the new species *Pseudomonas* BR11571 has a lot of advantageous characteristics, for example (a) being able to extract precious metals from secondary resources such as industrial residues and waste materials;

(b) producing biogenic substances facilitating the solubilization of precious metals; and (c) belonging to risk group 1.

Biogenic substances in general are substances produced by life processes. In the present invention a biogenic substance is any substance produced by the new species *Pseudomonas* BR11571. In a preferred embodiment according to the invention the biogenic substances comprise hydrocyanic acid.

In one embodiment according to the invention the biogenic substances are produced in the presence of amino acids. In a most preferred embodiment according to the invention the biogenic substances are produced in the presence of glycine. In a preferred embodiment according to the invention biogenic substances comprising hydrocyanic acid are produced in the presence of amino acids. In a most preferred embodiment according to the invention biogenic substances comprising hydrocyanic acid are produced in the presence of glycine.

As used herein, the singular form "a," "an," and "the" include plural references unless the context clearly dictates otherwise. For example, the term "a compound" or "at least one compound" may include a plurality of compounds, including mixtures thereof. Thus, for example, reference to "solid material," "the solid material," or "a solid material" also includes a plurality of solid materials; use of the term "a nucleic acid" optionally includes, as a practical matter, many copies of that nucleic acid molecule.

As used herein, the term "about" indicates that a value includes the inherent variation of error for the method being employed to determine a value, or the variation that exists among As used herein the terms "species", "strain" (with regard to *Pseudomonas* BR11571) and "*Pseudomonas* BR11571" can be used synonymously since the terms all relate to *Candidatus Pseudomonas metallosolvens* (having Accession Deposit Number DSM 32538.

FIGURES

FIG. 2: shows sequence similarity (expressed as percentage) of partial gene sequences (675 nt) of housekeeping gene gyrB (program arb, filter cFN55420 675 nt, Ludwig et al., 2004).

FIG. 6: shows the average nucleotide identity based on BLAST algorithm (ANIb). ANIb analysis (percentage identity) was performed using program PYANI (Pritchard et al. (2016)).

METAL RECOVERY

While *Pseudomonas* BR11571 according to the invention is basically also useful for leaching ores, the focus lies on solid materials containing precious metals, particularly gold and silver, but also platinum, palladium, rhodium, iridium and their mixtures. The microorganisms are also suitable for leaching copper, which is not typically counted among the term precious metal. Therefore the term "precious metal" includes gold, silver, platinum, palladium, rhodium, iridium, copper and their mixtures.

The term "secondary resources" means industrial residuals or waste materials, often contaminated with PCB and other organic material. Preferred suitable secondary resources are according to the present invention fly ashes, waste incineration ashes, metal scoriae, electronic scraps and the like.

Biocyanide:

The ability of *Pseudomonas* BR11571 to extract precious metals from solid resources is mainly attributed to the production of hydrocyanic acid in the presence of amino acids, in particular glycine. Besides, however, other biogenic substances are produced which facilitate the solubilization of precious metals. This leads to the surprising effect associated with the present invention that less (bio-) cyanide is required than in an abiotic, chemical process known from the state of the art.

*Pseudomonas* Br11571:

According to the invention, *Pseudomonas* BR11571 is provided as a new organism. This organism can be used to extract precious metals from solid materials. Surprisingly, this organism is able to extract precious metals also from materials that contain elevated levels of toxic metals such as lead, chromium, cadmium and silver. This allows the conclusion that the organism is not only able to extract precious metals from solid materials but has also a high tolerance against external conditions.

Figure 1:
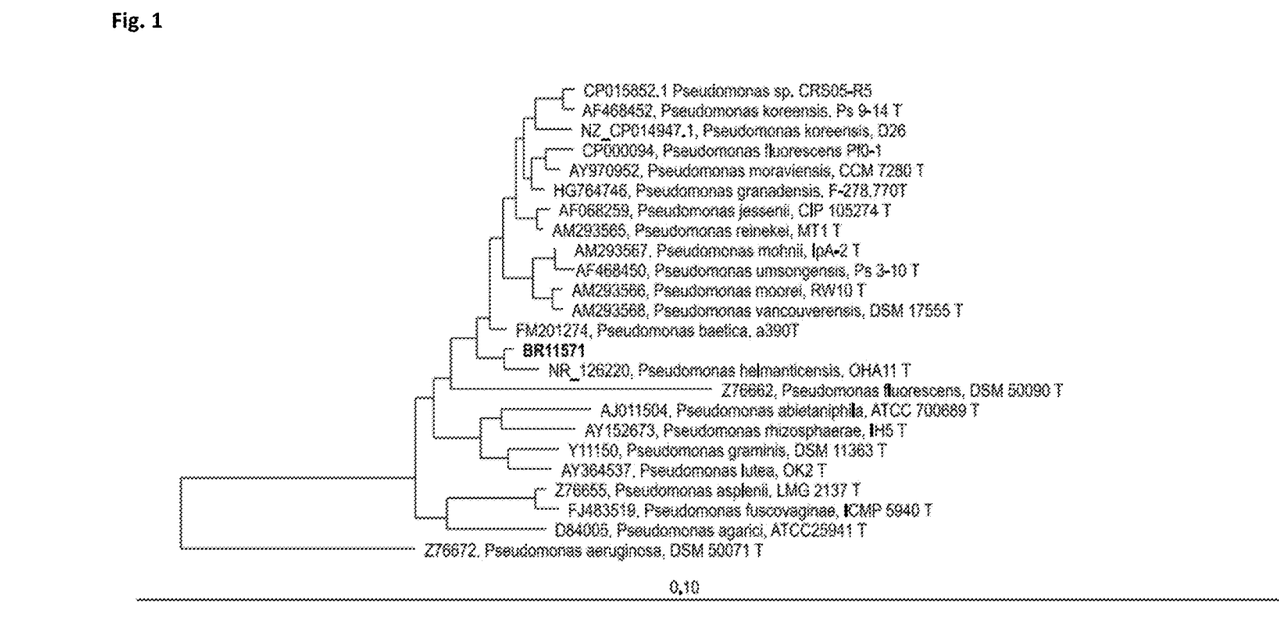
FIG. 1: is a distance matrix which was calculated by the Jukes-Cantor correction method using filter cBR11571 (*E. coli* position 100 to 1465 using arb-program, Ludwig et al., 2004) based on partial 16S rRNA gene sequences. Tree Dendrogram was generated by neighbor joining method.

The affiliation of the new species to the genus *Pseudomonas* was revealed by performing 16S rRNA gene analysis (FIG. 1).

It has been found that *Pseudomonas* BR11571 represents a novel species of the genus *Pseudomonas*. Classification of *Pseudomonas* BR11571 to a novel species of genus *Pseudomonas* was supported by phenotypic (API, BIOLOG) and genotypic data (further phylogenetic analysis of partial sequences of the housekeeping genes rpoB, rpoD and gyrB and calculation of average nucleotide identity (ANI) based on BLAST algorithm using scaffold genomes. Strains with less than 94% ANI with regard to scaffold genome are regarded as new species of a genus (according to e.g. Richter and Rosselló-Móra, 2009). BLAST analysis of scaffold genome DNA sequences showed that the next neighbor to *Candidatus Pseudomonas metallosolvens* BR11571 shared a percentage of ANI of ca. 91%.

Furthermore, the physiology of *Pseudomonas* BR11571 was found to be distinct from *Pseudomonas* species known so far as indicated by the API (Biomerieux API 20 NE) and BIOLOG (BIOLOG PM1, PM2A) assays.

The closest relatives of *Pseudomonas* BR11571 as revealed by partial sequence analysis of housekeeping genes rpoD, rpoB and gyrB and ANI analysis using scaffold genomes are *P. helmanticensis* OHA11 (Type strain), *P. granadensis* F-278,770 (Type strain) and *P. koreensis* DSM16610 (Type strain), all belonging to risk group 1 (FIGS. 2 to 6). Furthermore, 16S rRNA and partial sequence analysis as described above showed that *Pseudomonas* BR11571 belongs to *Pseudomonas koreensis* subgroup within the *Pseudomonas fluorescens* complex (Garrido-Sanz et al., 2016). Known type strains affiliated with *Pseudomonas koreensis* subgroup (Mulet et al., 2010) have been classified into risk group 1. Therefore, the new species *Candidatus Pseudomonas* BR11571 can be classified as risk group 1.

Deposit of Biological Material:

The isolated and identified species *Pseudomonas* BR11571 was deposited on Jun. 13, 2017, under the provisions of the Budapest Treaty in the Leibniz Institute DSMZ—German Collection of Microorganisms and Cell Cultures. It has been assigned to the Accession number DSM 32538.

In a preferred embodiment according to the invention, the new species belongs to risk group 1. The term "risk group" is a classification system which is used in many countries for the classification of microorganisms. The affiliation to a risk group depends for example on the following factors Pathogenicity of the organism Mode of transmission and host range Availability of effective preventive measures (e.g. vaccines)

Availability of effective treatment (e.g. antibiotics)

All microorganisms which belong to risk group 1 are not associated with disease in healthy adult humans (see NIH Guidelines in Recombinant DNA, April 2002).

In an embodiment according to the invention the ribosomal DNA of *Pseudomonas* BR11571 has SEQ ID No. 1.

As mentioned above, *Pseudomonas* BR11571 according to the invention is capable of producing biogenic substances. These biogenic substances produced by the *Pseudomonas* BR11571 facilitate the solubilization of precious metals from solid materials in the presence of amino acids. In a preferred embodiment according to the invention the biogenic substance produced by *Pseudomonas* BR11571 is hydrocyanic acid. In a further preferred embodiment the amino acid is glycine. In a most preferred embodiment according to the invention hydrocyanic acid is produced by *Pseudomonas* BR11571 which facilitates the solubilization of precious metals from solid materials in the presence of glycine.

Use:

In one embodiment according to the invention *Pseudomonas* BR11571 is used for extracting precious metals from solid materials. In a preferred embodiment according to the invention the solid material is a secondary resource. In a further preferred embodiment according to the invention the solid material is selected from the group consisting of fly ashes, waste incineration ashes, metal scoriae and electronic scraps.

Preferably the precious metals are selected from the group consisting of gold, silver, platinum, palladium, rhodium, iridium, copper and their mixtures.

Composition:

A further embodiment according to the invention relates to a composition comprising:

(a) *Pseudomonas* BR11571 in amounts effective to facilitate the solubilization of precious metals by releasing biogenic substances;

(b) at least one solid material; and (c) at least one amino acid.

In a preferred embodiment the at least one amino acid is glycine. In a further preferred embodiment according to the invention the biogenic substance comprises hydrocyanic acid.

Method:

One embodiment according to the invention relates to a method for extracting precious metals from solid material with *Pseudomonas* BR11571. In a preferred embodiment the solid material used in the method is a secondary resource. In a more preferred embodiment the solid material is selected from the group consisting of fly ashes, waste incineration ashes, metal scoriae and electronic scraps.

In a further preferred embodiment according to the method of the present invention the precious metals are selected from the group consisting of gold, silver, platinum, palladium, rhodium, iridium, copper and their mixtures.

In an embodiment according to the method of the present invention *Pseudomonas* BR11571 produces biogenic substances in the presence of amino acids which facilitate the solubilization of precious metals from solid materials. In a preferred embodiment according to the method of the present invention the biogenic substance released by *Pseudomonas* BR11571 comprises hydrocyanic acid. In a further preferred embodiment according to the method of the present invention the amino acid is glycine.

Isolated Nucleic Acid:

A further embodiment according to the invention relates to an isolated nucleic acid having at least 91% identity to SEQ ID No. 2.

In a preferred embodiment according to the invention the isolated nucleic acid having at least 92%, at least 93%, at least 94%, at least 95%, at least 96%, at least 97%, at least 98%, at least 99% identity to SEQ ID No. 2. In another preferred embodiment according to the invention the isolated nucleic acid having 100% identity to SEQ ID No. 2. In other words, the isolated nucleic acid is SEQ ID No. 2.

In a most preferred embodiment according to the invention the isolated nucleic acid having at least 94% identity to SEQ ID No. 2.

As used herein, the term "identity" when used in relation to nucleic acids, describes the degree of similarity between two or more nucleotide sequences. The percentage of "sequence identity" between two sequences can be determined by comparing two optimally aligned sequences over a comparison window, such that the portion of the sequence in the comparison window may comprise additions or deletions (gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa. An alignment of two or more sequences may be performed using any suitable computer program. For example, a widely used and accepted computer program for performing sequence alignments is CLUSTALW vl 0.6 (Thompson, et al. (1994) Nucl. Acids Res., 22: 4673-4680).

SEQ ID No. 2 represents an artificial sequence. This artificial sequence is the scaffold genome sequence of *Pseudomonas* BR11571. As used herein the term "scaffold" is a type of sequencing created by chaining contigs together using additional information about the relative position and orientation of the contigs in the genome. "Contigs" are continuous stretches of sequence containing only A, C, G, or T bases without gaps. Contigs in a scaffold are separated by gaps, which are designated by a variable number of 'N' letters.

EXAMPLES

Example 1: Isolation and Identification of *Pseudomonas* BR11571

*Pseudomonas* BR11571 was isolated according to the following procedure: plating a soil suspension in 0.85%

NaCl on 0.5×HD nutrient agar plates supplemented with 4 mM KCN and 100 µg/ml nystatin. Appearing microbial colonies were transferred and purified by a "clean streak" on fresh agar plates and subsequently analyzed for hydrocyanic acid production as well as for leaching efficiency of precious metals from secondary resource. Microorganisms that met the performance criteria were phylogenetically characterized by 16S rDNA analysis. The affiliation of strain BR11571 to the genus *Pseudomonas* was shown by performing 16S rRNA gene analysis of partial 16S rRNA gene sequences (FIG. 1) using program arb (Ludwig et al., 2004).

The strain was cultivated on LB medium (such as Bacto Tryptone #211705 (BD) 1% (w/v), Bacto Yeast Extract #212750 (BD) 0.5% (w/v), NaCl #141659.1221 (Applichem) 0.5% (w/v) and also mineral media such as M9 [according to: Harwood, C. R., and S. M. Cutting. 1990. Chemically defined growth media and supplements, p. 548. In C. R. Harwood and S. M. Cutting (ed.), Molecular biological methods for *Bacillus*. Wiley, Chichester, United Kingdom.] both supplemented with casamino acids (0.25%/w/v)) and glycine (0.5% (w/v)). Suitable incubation temperatures are preferably in the range of 28–30° C.

Figure 7:
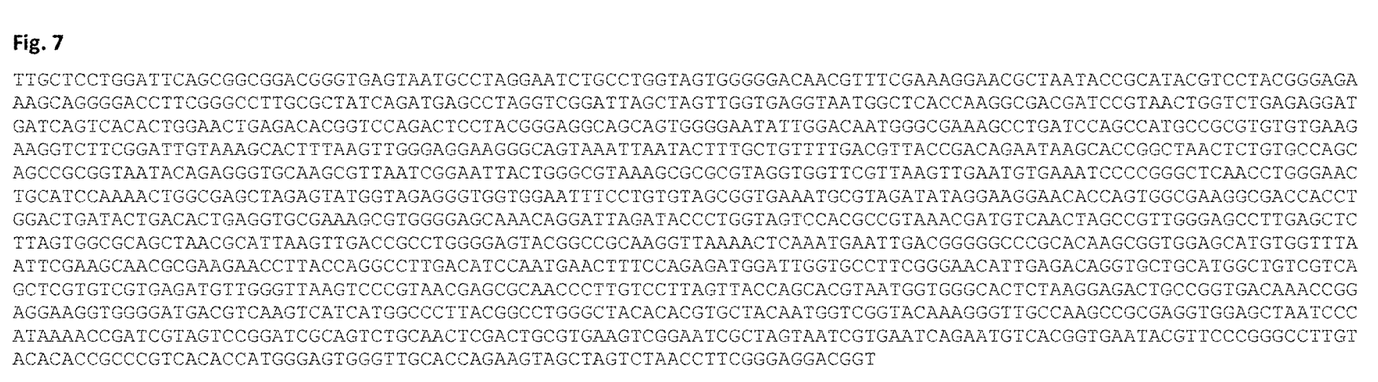
FIG. 7: shows the 16S rDNA sequence of *Pseudomonas* BR11571, which is SEQ ID No. 1.

The 16S rDNA sequence of *Pseudomonas* BR11571 is shown in FIG. 7 and SEQ ID No. 1. The isolated and identified strain has been submitted on Jun. 13, 2017 to the Leibniz Institute DSMZ—German Collection of Microorganisms and Cell Cultures. It has the accession number DSM 32538.

Example 2: Phylogenetic Analysis of *Pseudomonas* BR11571 and Definition of a New Group of Genus *Pseudomonas*

Figure 3:
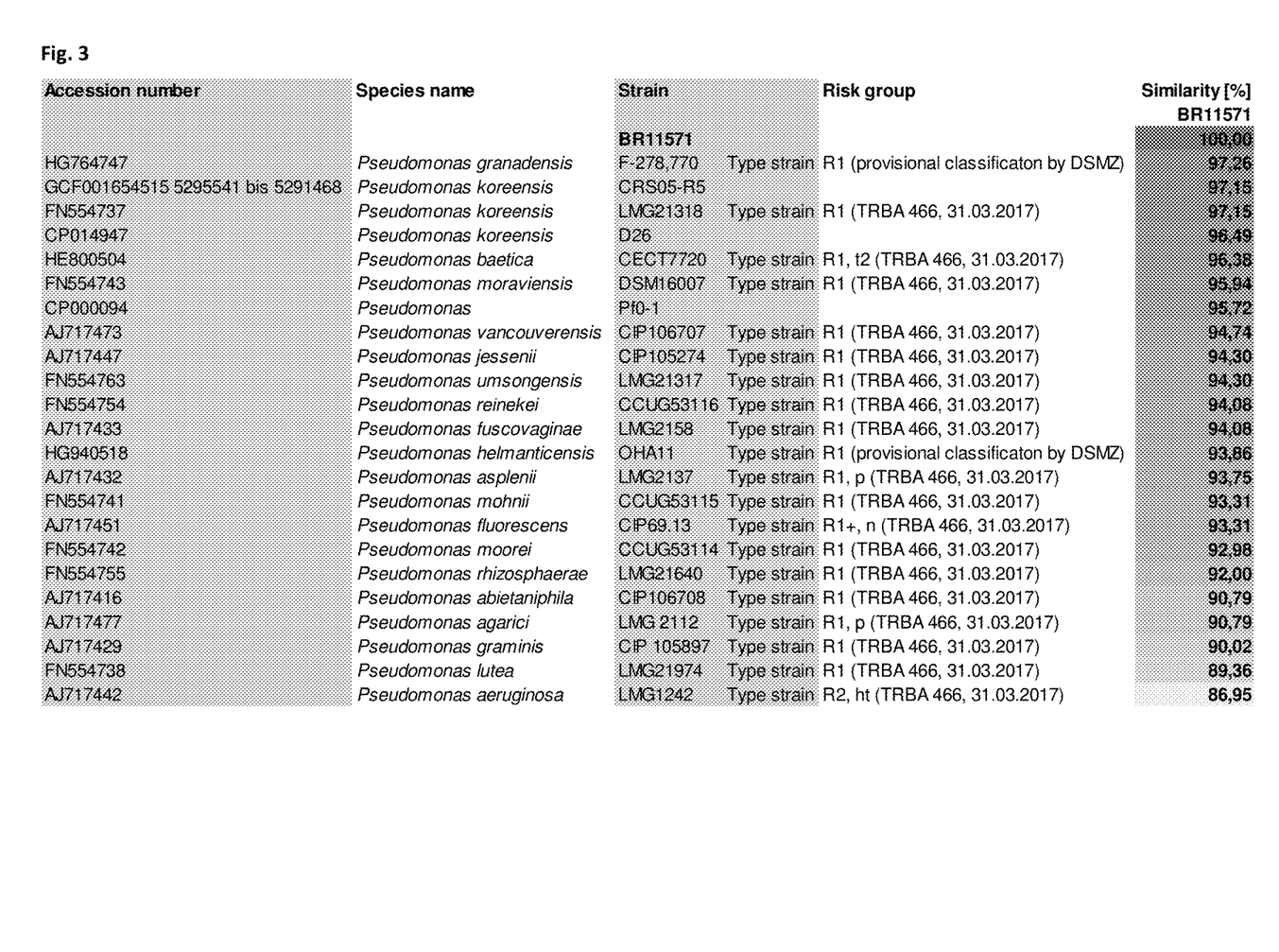
FIG. 3: shows sequence similarity (expressed as percentage) of partial gene sequences (912 nt) of housekeeping gene rpoB (program arb, filter SAI_AJ7174 912 nt, Ludwig et al, 2004).
Figure 4:
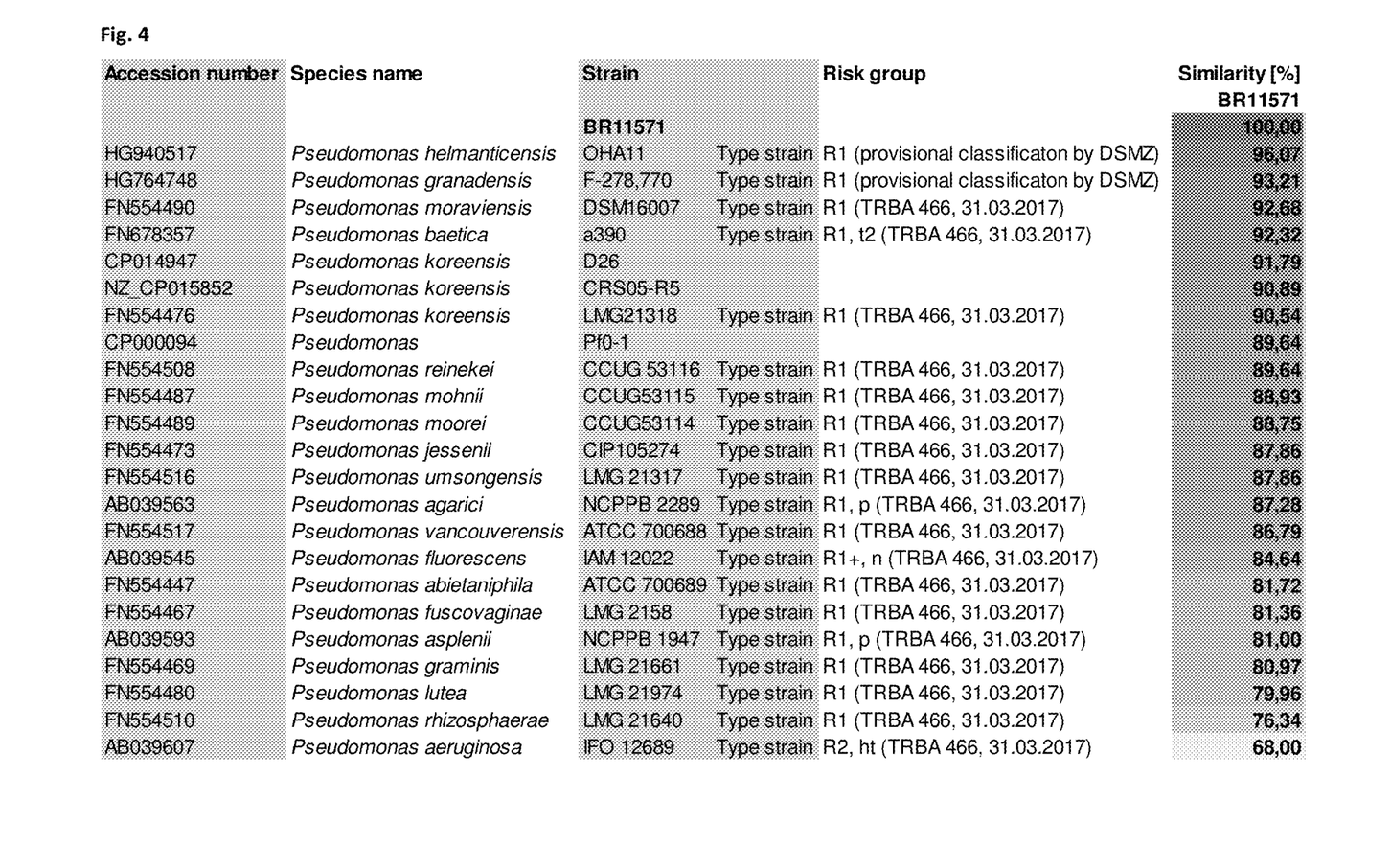
FIG. 4: shows sequence similarity (expressed as percentage) of partial gene sequences (560 nt) of housekeeping gene rpoD (program arb, filter cFM25190 560 nt Ludwig et al, 2004).
Figure 5:
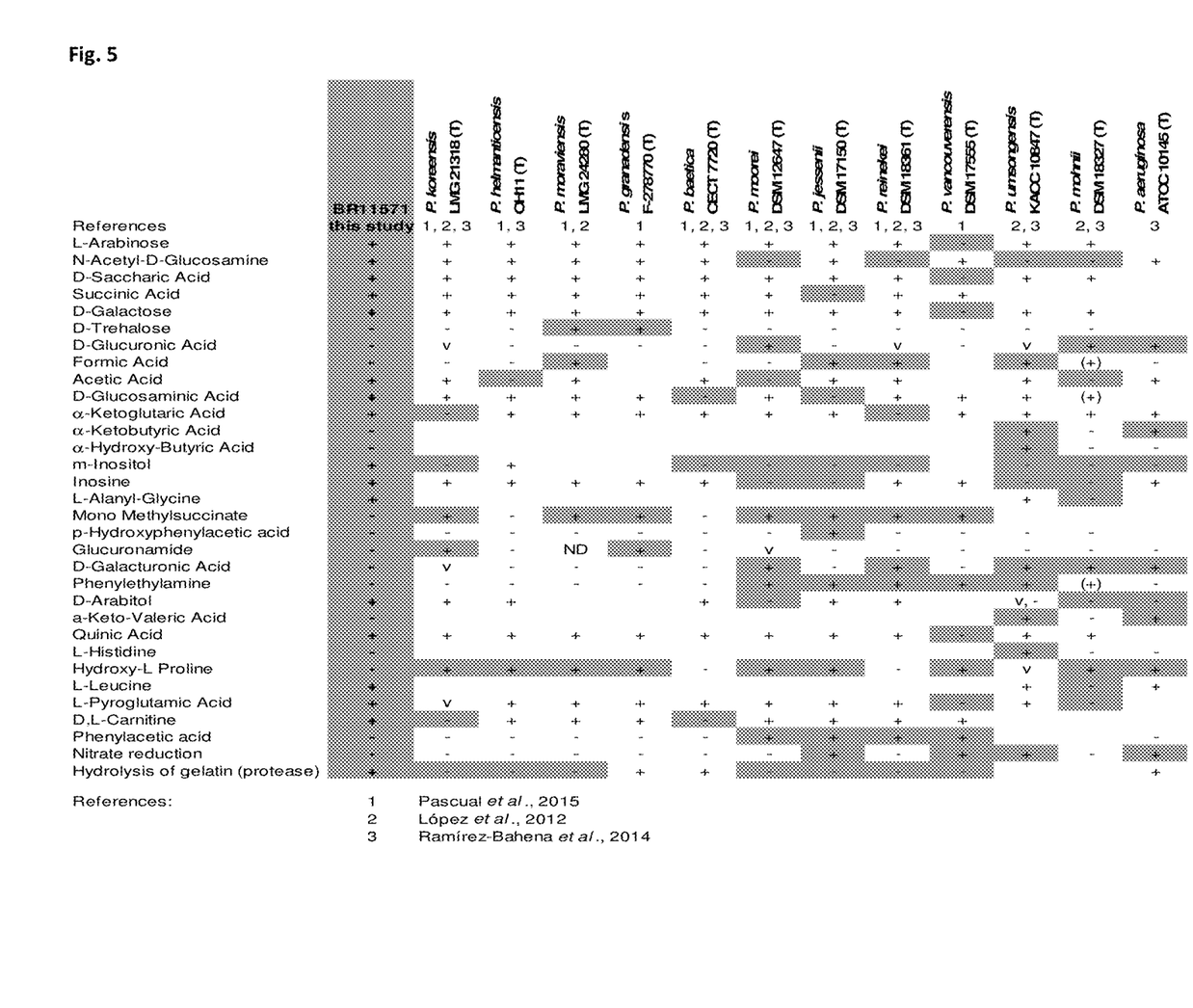
FIG. 5: shows analyzation of physiological traits of BR11571 with the standardized system for identification of non-fastidious, non-enteric Gram-negative rods that is API 20 NE (BIOMERIEUX) and carbon utilization tests based on BIOLOG PM1 and PM2A plates (BIOLOG) according to the manufacturer's instructions. Results were compared with selected results of relevant strains.

16S rRNA analysis of partial 16S rRNA genes revealed that BR11571 belongs to genus *Pseudomonas* (FIG. 1). Partial gene sequences of the housekeeping genes gyrB, rpoB and rpoD were analyzed to further investigate phylogenetic relationships of BR11571 (FIGS. 2-4). These four core "housekeeping" genes are usually used for analyzing *Pseudomonas* phylogeny (e.g. Mulet et al., 2010). A threshold of about 97% sequence similarity using these housekeeping genes has been suggested for species differentiation within the genus *Pseudomonas* (Mulet et al., 2010; Gomila et al., 2015). As is shown in FIG. 2, FIG. 3 and FIG. 4 maximal similarity values to closest related type strains are around 97%. These data suggest that *Pseudomonas* BR11571 is supposed to be a new species. To analyze physiological traits of BR11571 the standardized system for identification of non-fastidious, non-enteric Gram-negative rods that is API 20 NE (BIOMERIEUX) and carbon utilization tests based on BIOLOG PM1 and PM2A plates (BIOLOG) were used according to the manufacturer's instructions. Results were compared with selected results from literature of physiological tests of relevant strains. Relevant strains were chosen based on above phylogenetic sequence analysis results (FIG. 5). Analysis revealed that the physiology of *Pseudomonas* BR11571 is distinct from so far known *Pseudomonas* species as indicated by the API and BIOLOG assays (FIG. 5). These data further underline that *Pseudomonas* BR11571 can be classified as a novel species of the genus *Pseudomonas* termed *Candidatus Pseudomonas metallosolvens*.

DNA-DNA hybridization was substituted applying ANI analysis (e.g. Richter and Rosselló-Móra, 2009). The species level boundary proposed was set at about 94% ANI (e.g. Richter and Rosselló-Móra, 2009). As shown in FIG. 6 ANIb similarity values are below 91%. These results further underline that *Pseudomonas* BR11571 represents a novel species of the genus *Pseudomonas*. *Pseudomonas* strains sharing at least 94% ANI to scaffold genome of *Pseudomonas* BR11571 are regarded to be part of the new group of *Pseudomonas* (Goris et al., 2007)

Example 3: Recovery of Precious Metals Using *Pseudomonas* BR11571

Electronic scrap, i.e. printed card boards (PCB) was subjected to bioleaching using (a) *Pseudomonas* BR11571 (according to the invention)

(b) *Chromobacterium violaceum*, DSMZ 30191 (for comparison)

as heterotrophic microorganisms capable of producing and releasing hydrocyanic acid. The waste material with regard to metals mainly consisted of copper (6% b.w.), iron (6% b.w.), aluminum (4% b.w.) and zinc (2% b.w.). It also contained significant amounts of precious metal, particularly silver, gold and palladium.

Sample material was finely grinded in an impact mill. The resulting fine fraction (<1 mm) was used for leaching experiments. 1 g of this material was added to a leaching vessel having a volume of 0.3 l. The vessel was filled with 0.1 l of an aqueous solution comprising the microorganisms or (b), respectively in an amount of about 1 g/l wet weight, also containing minerals and carbohydrates in amounts suitable to serve as nutrients for the microorganisms. An amount of 0.5 g glycine was added to sustain hydrocyanic acid production. The mixture was heated to about 30° C. and agitated over a period of 120h at about 180 rpm. Subsequently, the slurry was collected by centrifugation and the liquid phase was analyzed for the amount of released precious metals and copper by ICP-MS analysis. Experiments were carried out in triplicate. The results are shown in Table 1.

TABLE 1

Recovery of precious metals from PCB

| | | Example 1 | |
|---|---|---|---|
| | Content [ppm] | Efficacy *C. violaceum* [%] | Efficacy BR11571 [%] |
| Ag | 713 | 2.8 ± 0.04 | 12.6 ± 3.4 |
| Au | 80 | 15.4 ± 0.8 | 20.3 ± 4.2 |

*Pseudomonas* BR11571 shows a 5-fold increased leaching efficiency of silver and 30% better leaching of gold than *Chromobacterium violaceum*. Furthermore, *Pseudomonas* BR11571 belongs to risk group 1, while *Chromobacterium violaceum* belongs to risk group 2, compromising the use of the latter microorganisms in an economically viable, industrial set-up.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11261218B2). An electronic copy of the "Sequence Listing" will also be available from the USPTO upon request and payment of the fee set forth in 37 CFR 1.19(b)(3).

The invention claimed is:

1. A composition comprising:
    (a) a species of genus *Pseudomonas* identified as *Pseudomonas* BR11571, having Accession Deposit Number DSM 32538 in amounts effective to facilitate the solubilization of precious metals by releasing biogenic substances;
    (b) at least one solid material; and
    (c) at least one amino acid.

2. The species according to claim 1, wherein said species belongs to risk group 1.

3. The species according to claim 1, wherein the ribosomal DNA of said species has SEQ ID No. 1.

4. The species according to claim 1, wherein said species is capable of producing biogenic substances.

5. A method comprising using a species of genus *Pseudomonas* identified as *Pseudomonas* BR11571, having Accession Deposit Number DSM 32538 for extracting precious metals from solid materials.

6. The method according to claim 5, wherein the solid material is a secondary resource.

7. The method according to claim 6, wherein the secondary resource is selected from the group consisting of fly ashes, waste incineration ashes, metal scoriae and electronic scraps.

8. The method according to claim 5, wherein the precious metals are selected from the group consisting of gold, silver, platinum, palladium, rhodium, iridium, copper and their mixtures.

9. The method according to claim 5, wherein the species produces biogenic substances which facilitate the solubilization of precious metals from solid materials.

10. The method according to claim 9, wherein the species produces biogenic substances in the presence of amino acids.

11. The method according to claim 9, wherein the biogenic substance comprises hydrocyanic acid.

12. The composition according to claim 1, wherein the at least one solid material (b) is selected from the group consisting of fly ashes, waste incineration ashes, metal scoriae and electronic scraps.

13. The composition according to claim 1, wherein the precious metals are selected from the group consisting of gold, silver, platinum, palladium, rhodium, iridium, copper and their mixtures.

14. The composition according to claim 1, wherein the at least one amino acid (c) is glycine.

* * * * *